(12) United States Patent
Kuo (10) Patent No.: US 9,820,829 B2
(45) Date of Patent: Nov. 21, 2017

(54) DENTAL POSITIONING APPLIANCE HAVING METALLIC PORTION

(71) Applicant: Align Technology, Inc., San Jose, CA (US)

(72) Inventor: Eric E. Kuo, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 222 days.

(21) Appl. No.: 14/578,244

(22) Filed: Dec. 19, 2014

(65) Prior Publication Data

US 2016/0175070 A1 Jun. 23, 2016
US 2017/0189140 A9 Jul. 6, 2017

Related U.S. Application Data

(63) Continuation of application No. 13/431,783, filed on Mar. 27, 2012, now Pat. No. 8,944,812, which is a continuation of application No. 12/247,559, filed on Oct. 8, 2008, now Pat. No. 8,152,518.

(51) Int. Cl.
*A61C 7/08* (2006.01)
(52) U.S. Cl.
CPC .......... *A61C 7/08* (2013.01); *A61C 2201/007* (2013.01); *Y10T 29/49568* (2015.01)
(58) Field of Classification Search
CPC ................ A61C 2201/007; A61C 7/08; Y10T 29/49568
See application file for complete search history.

(56) References Cited

U.S. PATENT DOCUMENTS

| | | | | |
|---|---|---|---|---|
| 3,089,487 A * | 5/1963 | Enicks | ................. | A63B 71/085 128/861 |
| 3,955,282 A * | 5/1976 | McNall | ................... | A61C 7/12 433/9 |
| 4,055,895 A * | 11/1977 | Huge | ....................... | A61C 7/08 128/861 |
| 4,433,960 A * | 2/1984 | Garito | ...................... | A61C 7/00 433/180 |
| 4,793,803 A * | 12/1988 | Martz | ...................... | A61C 7/08 433/6 |
| 5,018,969 A * | 5/1991 | Andreiko | .................. | A61C 7/16 433/20 |
| 5,314,335 A * | 5/1994 | Fung | ........................ | A61C 5/00 433/218 |
| 5,344,315 A * | 9/1994 | Hanson | .................... | A61C 7/20 433/20 |
| 5,415,542 A * | 5/1995 | Kesling | .................... | A61C 7/08 433/6 |
| 6,183,248 B1 * | 2/2001 | Chishti | ................... | A61C 7/00 433/24 |
| 6,524,101 B1 * | 2/2003 | Phan | ....................... | A61C 7/00 433/24 |

(Continued)

*Primary Examiner* — Jacob Cigna
(74) *Attorney, Agent, or Firm* — Brooks, Cameron & Huebsch, PLLC (57) ABSTRACT

Embodiments are provided for utilizing metallic portions in dental positioning appliances. One embodiment includes a removable dental positioning appliance having a shell having one or more cavities shaped to receive and reposition one or more teeth from a first orientation to a successive orientation and where at least a portion of the shell is formed from a metallic mesh material.

15 Claims, 5 Drawing Sheets

(56) References Cited

U.S. PATENT DOCUMENTS

| | | | | |
|---|---|---|---|---|
| 2001/0041320 A1* | 11/2001 | Phan | ........................ | A61C 7/00 |
| | | | | 433/6 |
| 2003/0224311 A1* | 12/2003 | Cronauer | ................. | A61C 7/08 |
| | | | | 433/6 |
| 2004/0152036 A1* | 8/2004 | Abolfathi | ................. | A61C 7/00 |
| | | | | 433/24 |
| 2004/0209218 A1* | 10/2004 | Chishti | .................... | A61C 7/00 |
| | | | | 433/6 |
| 2005/0186524 A1* | 8/2005 | Abolfathi | ................. | A61C 7/10 |
| | | | | 433/7 |
| 2008/0254403 A1* | 10/2008 | Hilliard | ................... | A61C 7/20 |
| | | | | 433/24 |
| 2010/0086890 A1* | 4/2010 | Kuo | ........................ | A61C 7/08 |
| | | | | 433/6 |

* cited by examiner

DENTAL POSITIONING APPLIANCE HAVING METALLIC PORTION

CROSS-REFERENCE TO RELATE TO RELATED APPLICATIONS

This application is a continuation of U.S. patent application Ser. No. 13/431,783, filed on Mar. 27, 2012, which is a continuation of U.S. patent application Ser. No. 12/247,559, filed Oct. 8, 2008, now issued as U.S. Pat. No. 8,152,518, the entire contents of which are hereby incorporated by reference.

BACKGROUND

The present disclosure is related generally to the field of orthodontics. More particularly, the present disclosure is related to a dental positioning appliance having one or more metallic portions.

Many orthodontic treatments involve repositioning misaligned teeth and changing bite configurations for improved dental function and cosmetic appearance. Repositioning can be accomplished, for example, by applying controlled forces to one or more teeth over a period of time.

Some orthodontic processes use removable positioning appliances for realigning teeth. Such appliances may utilize a thin shell of material having resilient properties, (an individual appliance is referred to as an "aligner") whereby each appliance generally conforms to a patient's teeth but is slightly out of alignment with the initial tooth configuration.

Placement of such an appliance over the teeth can provide controlled forces in specific locations to gradually move the teeth into a new configuration. Repetition of this process with successive appliances that provide progressive configurations eventually move the teeth through a series of intermediate arrangements to a final desired arrangement. An example of such a system is described in U.S. Pat. No. 5,975,893.

Such systems typically utilize materials that provide light weight and/or transparent appliances in a set that can be used serially such that as the teeth move, a new appliance can be implemented to further move the teeth. Such features may be beneficial in many instances, however, in some instances, it may be desirable to provide movement with less appliances, thereby reducing modeling and manufacturing costs as well as reducing the number of appliances the user has to utilize and keep track of, among other benefits. Additionally, if the appliance is designed to treat a smaller number of teeth within a patient's mouth, then it may be difficult to create a sufficient anchoring force or motive force with a plastic material used to form many such appliances that would be used to make the movements to the teeth that are desired.

DETAILED DESCRIPTION

According to the present disclosure, appliances and methods are provided for utilizing metallic portions in dental positioning appliances. In some embodiments, a removable dental positioning appliance has a shell with one or more cavities shaped to receive and reposition one or more teeth from a first orientation to a successive orientation and where at least a portion of the shell is formed from a metallic material (e.g., metallic mesh material). In various embodiments, the shell can be shaped to accommodate one tooth or multiple adjacent or nonadjacent teeth based upon the number and position of the one or more cavities that form the one or more portions of the shell.

Figures 1A, 1B:
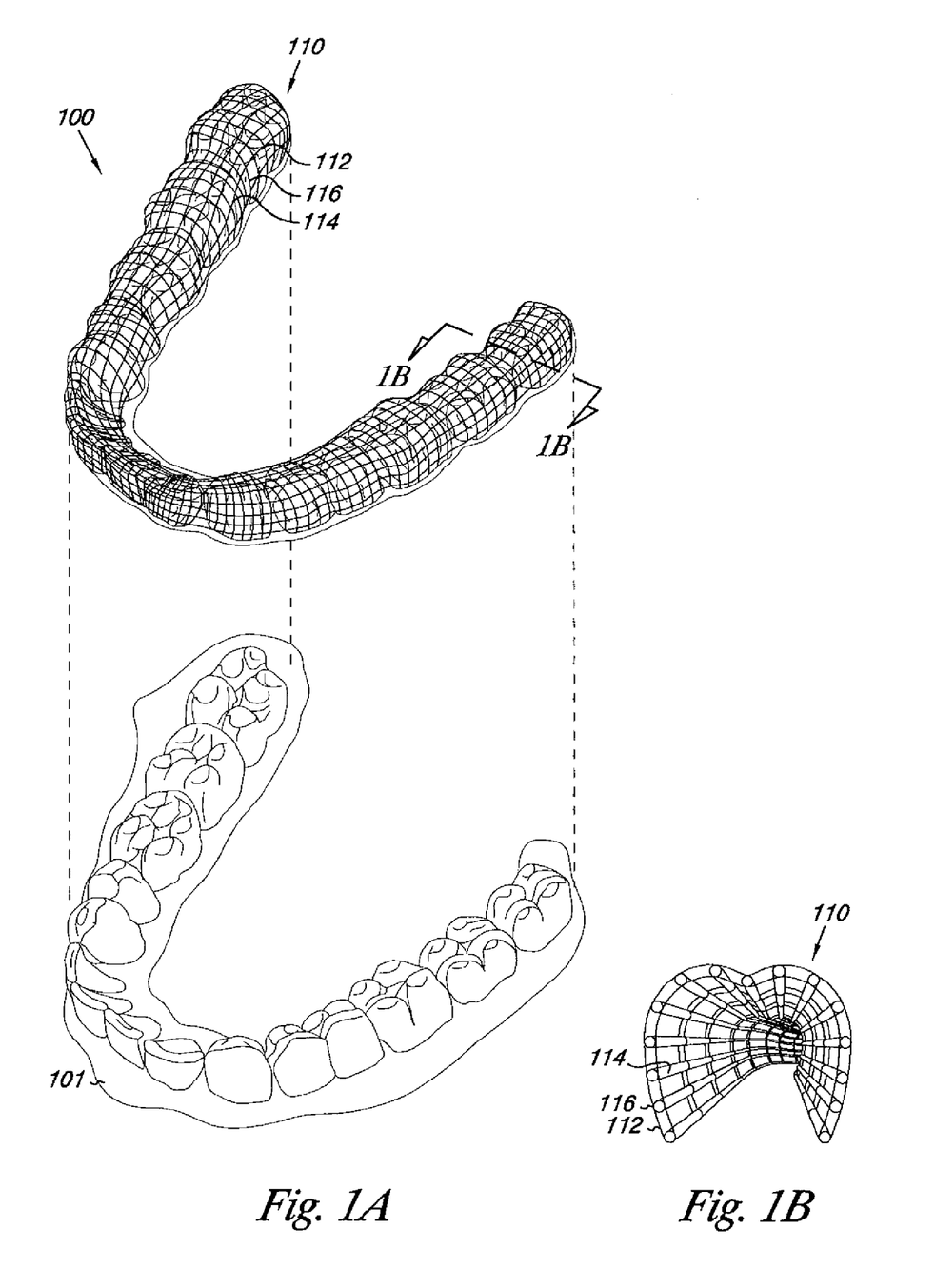
FIG. 1A illustrates a lower jaw of a subject together with an example of a dental positioning adjustment appliance embodiment according to the present disclosure.
FIG. 1B illustrates a cut away view of the appliance of FIG. 1A taken along line 1B-1B.

FIG. 1A illustrates a lower jaw of a subject together with an example of a dental positioning adjustment appliance embodiment according to the present disclosure. In the embodiment of FIG. 1A, the appliance 100 includes a mesh made out of a metallic material 110.

In various embodiments, the metallic material can be a planar sheet of material, strips of material, or one or more wires, among other material configurations and can be in a mesh, solid, perforated, layered, adjacently oriented, or other type of configuration. In the embodiment of FIG. 1A, the appliance is formed by one or more wires arranged in an overlapping pattern to form a mesh.

In some embodiments, a single wire can be woven to form the mesh. In the embodiment illustrated in FIG. 1A, multiple vertical wires 112 are provided. In the embodiment illustrated in FIG. 1A, multiple horizontal wires 114 are also provided. In various embodiments, as shown in the embodiment of FIG. 1A, the wires can be laid over each other and/or woven together.

As will be discussed in greater detail herein, the wires can be unfastened or can be fastened together in various manners. For example, the wires can be frictionally held together such as by weaving or tying, or held together by another material, such as solder, plastic, and/or an adhesive material among other suitable materials. In some embodiments, these materials can be coated onto or encapsulating around a portion of (e.g., such as the junctions 116 or other portions of wires 112 and 114 of the embodiment of FIG. 1A) or an entire wire or the mesh as will be discussed in more detail herein.

The methods of the present disclosure can employ any positioners, retainers, and/or other removable appliances for finishing and maintaining teeth positions in connection with orthodontic treatment. The systems for use with embodiments of the present disclosure provide a plurality of such appliances can be intended to be worn by a patient successively in order to achieve the gradual tooth repositioning as described herein.

In such embodiments, such as that shown in FIG. 1, an appliance 100 can, for example, be fabricated from a shell having at least a portion formed from a metallic material. In various embodiments, the metallic material can be utilized to provide a resilient functionality sufficient to move at least one tooth.

In the embodiment of FIG. 1A, the metallic portion is utilized to form a cavity shaped to receive and resiliently reposition one or more teeth from one teeth arrangement to a successive teeth arrangement. The shell may be designed to fit over a number of, in many instances all teeth, present in the upper or lower jaw 101.

In some situations, certain individual or small sets of the teeth can be repositioned while others of the teeth can be used to provide a base or anchor region for holding the repositioning appliance in place as it applies the resilient repositioning force against the tooth or teeth to be repositioned. In some embodiments, the metallic portion of the shell can be oriented to provide additional support with respect to holding the appliance in place. Such embodiments can aid in stabilizing one or more teeth.

Such orientation can be beneficial, for example, where the tooth or teeth used as an anchor may have been recently moved and may not provide as much support as teeth that have not been moved. Such orientation can also be beneficial, for example, where a larger anchoring force may be needed than can typically be provided by the number of teeth being used as the anchor. In such instances, the metallic portion can be placed at or near the tooth or teeth used for anchor to provide support and/or force to provide the anchoring functionality.

In various embodiments, the metallic portion of the appliance can be oriented to provide the repositioning force whereby a plastic shell portion of the appliance provides a stabilizing anchoring support for the device. This orientation enables the conformation of the shell portion to adapt to the anchoring teeth and depending on the metal properties selected, a greater effective range for force generation on the repositioning portion of the appliance.

FIG. 1B illustrates a cut away view of the appliance of FIG. 1A taken along line 1B-1B. In this illustration, the mesh structure of the embodiment of FIG. 1A can be observed more closely.

In the embodiment of FIG. 1B, the appliance 100 includes a number of wires forming a mesh pattern 110. The wires illustrated in FIG. 1B include a number of generally vertical wires 112 and a number of generally horizontal wires 114.

In various embodiments, the wires may be in different orientations, such as, but not limited to, non-horizontal and/or non-vertical, and/or irregular. Further, in some embodiments, the wires may be non-linear. For example, a wire may be bent in one direction (e.g., one axis with respect to an axis of the elongation direction of the wire), as shown with respect to wires 112 in FIG. 1B, or more than one direction (e.g., in two axial directions with respect to the axis of elongation of the wire).

The wires may include alternating active and passive wires, in some embodiments. In other words, varying wire materials may be present within the mesh.

Non-metallic wires may be incorporated into the mesh for additional support or improved esthetics, among other benefits. For example, metal fibers may be alternated with composite fibers to create a hybrid mesh.

In the embodiment illustrated in FIG. 1B, the vertical wires 112 are layered over the horizontal wires 114. As stated above, however, in various embodiments, the wires (e.g., 112 and 114) may be woven together such as in an alternating over-under type pattern.

In embodiments, such as that shown in FIG. 1B, the wires form a number of junctions 116 where the wires cross each other. As discussed above, the wires can, in some embodiments, be fastened together at these junction points. The fastening can be accomplished, for example, by a mechanical bracket type fastener, tied together, or by some type of bond being formed. Bonding mechanisms can include, for example, resins, adhesives, solder, polymers, and other materials that can be used to connect two wires together.

Figures 2A, 2B, 2C:
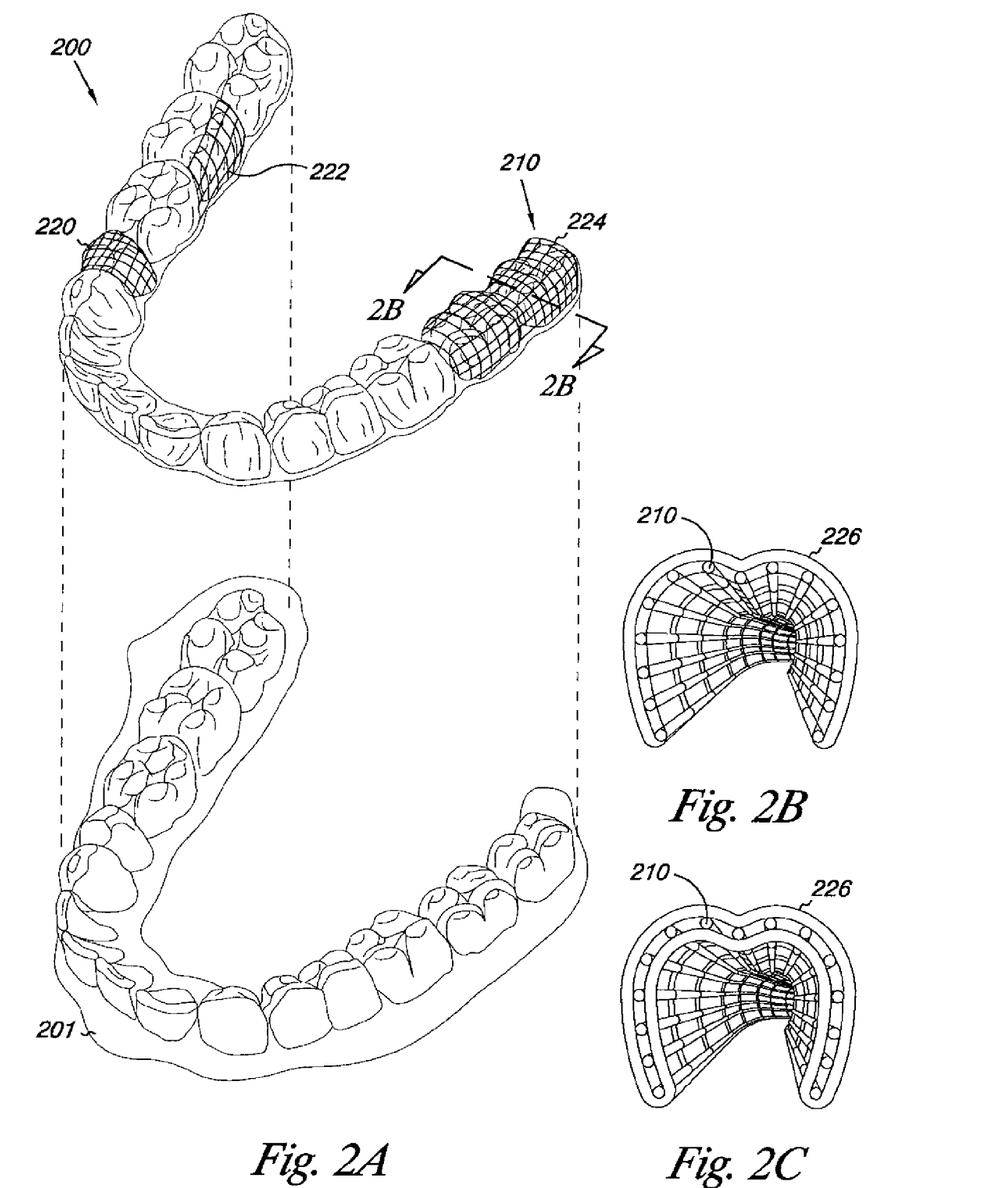
FIG. 2A illustrates a lower jaw of a subject together with an example of several dental positioning adjustment appliance embodiments according to the present disclosure.
FIG. 2B illustrates a cut away view of one of the appliance embodiments of FIG. 2A taken along line 2B-2B.
FIG. 2C illustrates a cut away view of another appliance embodiment taken along a similar line as FIGS. 1B and 2B.

FIG. 2A illustrates a lower jaw 201 of a subject together with an example of several dental positioning adjustment appliance embodiments according to the present disclosure. In the embodiment of FIG. 2A, the appliance 200 includes a number of metallic portions 220, 222, and 224. In some embodiments, these portions could each be a separate (or part of a separate) dental appliance.

In the embodiment of FIG. 2A, the portions 220, 222, and 224 are part of a one piece shell 200 that has other portions formed from an other material than the metallic material of portions 220, 222, and 224. In the embodiment of FIG. 2A, the metallic material is a mesh material 210 which can, for example, be formed by wires or strips of material, by a sheet of material with holes punched therein, or in other manners. The other material described above can be any suitable material for coating and/or connecting to the one or more metallic portions 220, 222, and/or 224.

The embodiment of FIG. 2A includes tooth structures 220 and 224 that where each of the teeth is reinforced with metallic material 210 that spans at least the buccal and mesial surfaces. Such embodiments can be useful for a variety of purposes. For example, the mesh material can be used to further aid in anchoring a tooth.

The mesh material can be used to apply extra force to a particular tooth and/or to extend the ability of the appliance to move the tooth. Depending upon the type of material used to form the mesh, the distance of the movement of the tooth can be elongated, because the force imparted by the metallic material may be over a greater distance than other materials, such as some polymers and other materials.

In various embodiments, the length of time that the movement can take place can be elongated because the metallic material may not lose its ability to impart force as readily as some other materials, such as some polymers and other materials. In some embodiments, the length of time that movement of a tooth takes may be reduced because the metallic material can impart either a greater force or more consistent force over a greater range of movement than some other materials, such as some polymers.

In the embodiment of FIG. 2A, a portion includes a metallic material. In this embodiment, the portion 222 includes a metallic mesh material that is provided on a surface (e.g., lingual) that is typically not visible to a person looking at the patient's mouth and therefore, this may be a desirable embodiment for such situations. The use of a metallic portion on one or more selected surfaces, such as is shown in the portion 222 of the embodiment of FIG. 2A can also be used, for example, to impart a particular force on the tooth (e.g., anchoring force, movement force, etc.). It should be noted that in some embodiments, the metallic material can be placed between two teeth which may provide an anchoring force or movement force to one or both of the teeth.

In some embodiments, as will be discussed in more detail herein, portions of or the entire appliance can be coated with a second material. This second material can be used to form the other portions (i.e., the portions other than 220, 222, and 224) of the dental appliance described above, in some embodiments.

In various embodiments, the second material could be a coating over, under, or encapsulating the portions 220, 222, and 224. Materials that can be used can include solders, epoxies, glues, polymers, oxides, and other suitable coating materials. In various embodiments, the materials may be bio-compatible materials.

Coatings can provide, for example, a more palatable texture, interaction with tooth surfaces, and/or taste than the metallic material, among other benefits. Another benefit may be that the coating can be used to hold one or more of the wires (e.g., wires 212 and 214 in the embodiment of FIG. 2A), forming the mesh, in place. Another benefit can be that a second material may be more pleasing to the eye than the metallic material and therefore, may be more desirable to be used in viewable areas of the oral environment, such as the buccal, occlusal, and/or mesial surfaces of a tooth or teeth, among other surfaces.

FIG. 2B illustrates a cut away view of one of the appliance embodiments of FIG. 2A taken along line 2B-2B. In the embodiment of FIG. 2B, the appliance includes a metallic mesh material 210 having a second material (e.g., a coating) 226 on the outside of the mesh portion 210.

In various embodiments, a second material can (i.e., in addition to the metallic material), for example, be placed at one or more junctions of the wires (e.g., junctions 116 of FIG. 1B), can be applied over (e.g., as illustrated in FIG. 2B at 226) or under portions or all of a wire or the mesh, or can be applied to encapsulate portions or all of a wire or the mesh. In some embodiments, this second material can be or include one or more agents that can be dispensed into the oral environment. It may be appreciated that any suitable agents, such as fluoride materials, antibiotics and/or antimicrobials and/or other chemicals, drugs, metallic ions, or medications, such as vitamins, bleaching materials, and/or breath fresheners, may be delivered to the oral environment in this manner.

In such embodiments, the second material may be oriented on the appliance such that it can be positioned proximate to an area needing such an agent. Accordingly, the second material can be selectively applied to particular portions of the appliance in such embodiments.

In various embodiments, the appliance may include one or more metallic portions and one or more non-metallic portions where at least one of the non-metallic portions forms part of the appliance body (e.g., where the appliance is part metallic and part polymeric) and at least one of the non-metallic portions is a coating formed over at least a portion of the body of the appliance (e.g., where an agent is applied over a portion of the metallic and/or polymeric portions of the appliance). In some embodiments, an agent can be impregnated into a material (e.g., a polymeric material) and can be released out of the material by interaction with the oral environment.

As illustrated in the embodiment of FIG. 2B, a coating can be applied over the metallic material. In some embodiments, a second material can be applied under the metallic material. Such embodiments can be beneficial, for example, where the metallic material may interfere with filling material, where tooth surfaces may be sensitive to metallic materials, and/or where it may be desirable to provide a softer and/or more uniform interface surface for contacting the surfaces of one or more teeth, among other benefits.

FIG. 2C illustrates a cut away view of another appliance embodiment taken along a similar line as FIGS. 1B and 2B.

In the embodiment of FIG. 2C, the metallic portion 210 is shown as being encapsulated within the second material 226.

Such embodiments can have one or more of the above recited benefits. It should be noted that such an illustration may be representative of an entire appliance that is fabricated from a metallic material and encapsulated within a second material or where a portion of an appliance is fabricated with a metallic material and where that portion is encapsulated.

For example, in some embodiments, the appliance may be formed mostly from a polymeric material and where a metallic material is encapsulated in a portion. Such embodiments may aid in reinforcing or providing additional force to a particular area.

The metallic material, such as a metallic mesh material can be formed by metal injection molding, by casting (which may include heat-treatment post-casting), by stamping the appliance using a stamp, by pressing and/or heat treating with a mold, or by bending individual metallic portions (e.g., wires) and/or soldering the individual wire components together, among other techniques. In some embodiments, the metallic material may be arch-preformed.

In some embodiments, the metallic material may be friction shaped through a pressing or other type of process wherein the material is shaped through a friction involving process. In various embodiments, the metallic material may be ultrasonically heated to maintain or obtain a desired shape.

In some embodiments, once the shape is formed, the metallic material can be coated with a second material. For example, in some embodiments, the coating can be sprayed or dip coated onto the metallic material. In various embodiments, the appliance can be cut (e.g., by a mechanical cutting tool or laser cutting tool) to trim the edges.

In some embodiments, the computing device executable instructions for the cutting tool may be programmed to cut at mesh junctions to avoid sharp points in the final product. In some embodiments, the appliance may be dipped in a coating to cover any sharp edges, among other sharp edge solutions.

Figure 3:
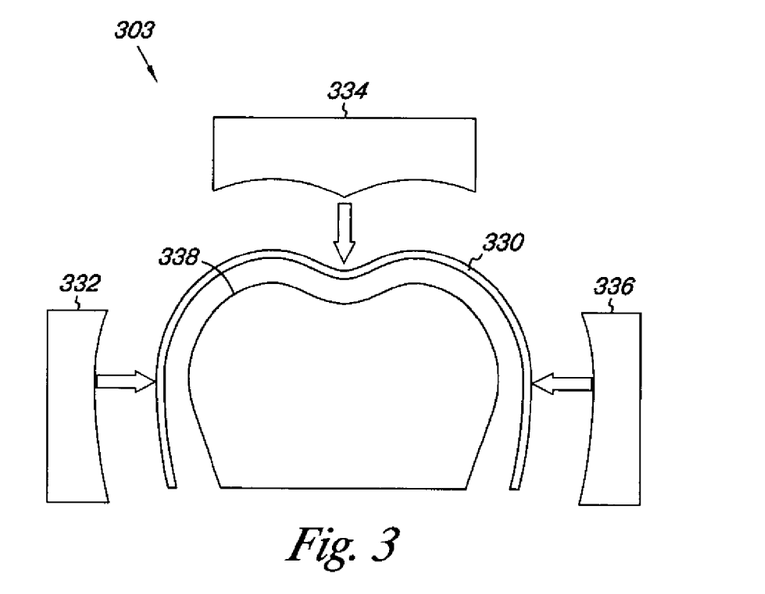
FIG. 3 illustrates an embodiment of a mechanism that could be used to form one or more appliance embodiments of the present disclosure.
Figure 4:
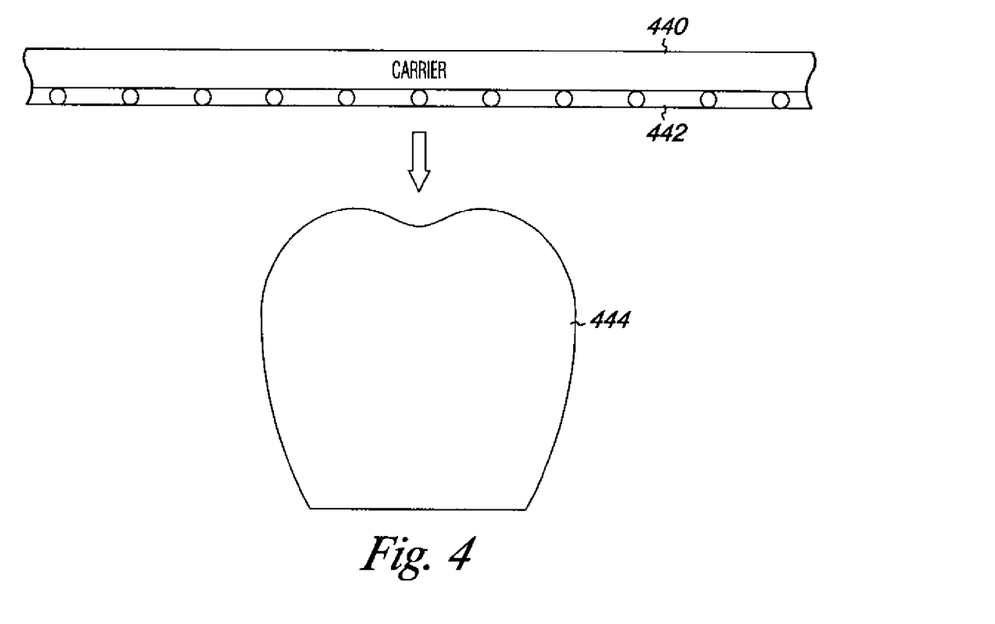
FIG. 4 illustrates a process for forming an appliance according to one or more embodiments of the present disclosure.

There are several processes that can be used to form the appliance or portion thereof having metallic material. FIGS. 3 and 4 illustrate two such ways and discussion is provided about some other processes that may be utilized.

FIG. 3 illustrates an embodiment of a mechanism that could be used to form one or more appliance embodiments of the present disclosure. In the embodiment of FIG. 3, a portion of a mechanism 303 is illustrated that can be used to form a portion of the shape of an appliance such as those illustrated in FIGS. 1A-2C.

FIG. 3 shows a cross-sectional view of the forming of an appliance from a metal sheet of material 330. It will be understood that this sheet of material could be a sheet of mesh material or other type of metallic or partially metallic material.

In a process such as that illustrated in FIG. 3, an appliance having metallic material can be pressed over a mold using a positive or, in some cases, a negative shape in a desired configuration. In some embodiments, metallic material can be sandwiched into a multi-piece forming mechanism (e.g., a number of dies), to press and/or hold the metallic material in a desired shape.

In the embodiment of FIG. 3, the forming mechanism 303 includes several portions, namely portions 332, 334, 336, and 338. These at least some of these portions move toward one another to bend the sheet of material 330.

In some embodiments, changes in temperature of the environment around the mechanism 303, of the portions 332, 334, 336, and/or 338 and/or the material 330 can be used to create the desired shape and/or force properties of the appliance or portion being formed. In various embodiments, some portion of the forming mechanism 303 or the entire mechanism can be formed from a metallic or ceramic material.

Where a shape memory type material is used as material 330, then, a change in temperature or stress can be applied to the material 330 to produce the desired shape and/or force characteristics of the appliance or portion being formed. For instance, in some embodiments, the metallic material can be a shape memory alloy formed at least in part from nickel, titanium, copper, aluminum, and/or zinc, among other materials.

In such embodiments and as stated above, the metallic material may be coated for esthetics and/or hygiene among other considerations. In such embodiments, the amount of movement built in can, for example, be based on the amount of distortion that can be tolerated to still ensure appliance fit.

FIG. 4 illustrates a process for forming an appliance according to one or more embodiments of the present disclosure. In the embodiment of FIG. 4, an appliance or portion thereof can be formed over a positive model 444 of a desired shape, using a carrier material 440 to enable formation of the metallic material (e.g., metallic mesh material) 442 around the desired shape 444. The metallic material 442 can then be set, for example, with high heat. The carrier material 440 can then be removed by any suitable manner.

One suitable manner, for example, may be that the carrier material 440 is a dissolvable material, which can be removed by dissolving with a solvent such as water, organic solvent, or other solvent types. In some embodiments, the carrier 440 may be a wax which can be melted or burned off.

Another process for creating appliance embodiments or portions thereof may be to bend the individual ribs in a mesh material and then to assemble the individual ribs with connecting wire and solder or otherwise attach the framework together.

Various embodiments of the present disclosure can enable a longer range of movement to be built into an appliance without increasing the amount of force placed on the teeth. In other words, through use of shape memory alloy materials, for example, it may be possible for an appliance to provide the movement of 5 to 10 polymeric appliances without increasing patient discomfort and/or negative biological effects of high force on the one or more teeth.

As a result of such embodiments, fewer appliances may have to be built, thereby reducing materials costs and/or visits to the treatment professional, among other benefits. Another possible benefit is because the material is metallic it may be easier to disinfect an appliance, in some instances.

Figure 5:
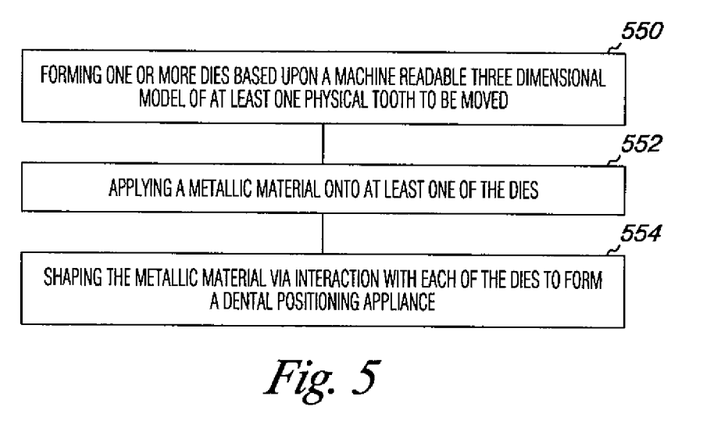
FIG. 5 illustrates a general method for forming an appliance according to one or more embodiments of the present disclosure.

FIG. 5 illustrates a method of forming a removable dental positioning appliance according to one or more embodiments of the present disclosure. In the embodiment of FIG. 5, the method includes forming one or more dies based upon a machine readable three dimensional model of at least one physical tooth to be moved, at block 550. A metallic material can be applied onto at least one of the dies, as provided in block 552.

The metallic material can be shaped via interaction with each of the dies to form a dental positioning appliance, at block 554. In this manner, the metallic appliance can be shaped to fit the intended user.

In various embodiments, one or more methods can include applying a metallic material that is a metallic mesh material. Applying the metallic material can include applying at least one wire.

Shaping the metallic material can include pressing the metallic material between at least two of the dies. In some embodiments, shaping the metallic material can include bending the metallic material into contact with at least one of the dies.

In some embodiments, a method can include applying a coating to at least a portion of the appliance. Method embodiments can also include heating the metallic material to change the material into a shape memory material.

In various embodiments, a method can include trimming one or more edges of the appliance. Methods can also include polishing one or more portions of the appliance. In some such embodiments, a method can include forming the shell into a dental positioning appliance or incorporating the shell into a dental positioning appliance.

In some embodiments, the appliance can be a mouth guard that protects teeth, but may or may not do any positioning of teeth. In such embodiments, the mouth guard can be coated with a thicker coating or the coating material can provide more shock absorption. Any suitable mouth guard features, design, or materials can be utilized with embodiments of the present disclosure.

Figure 6:
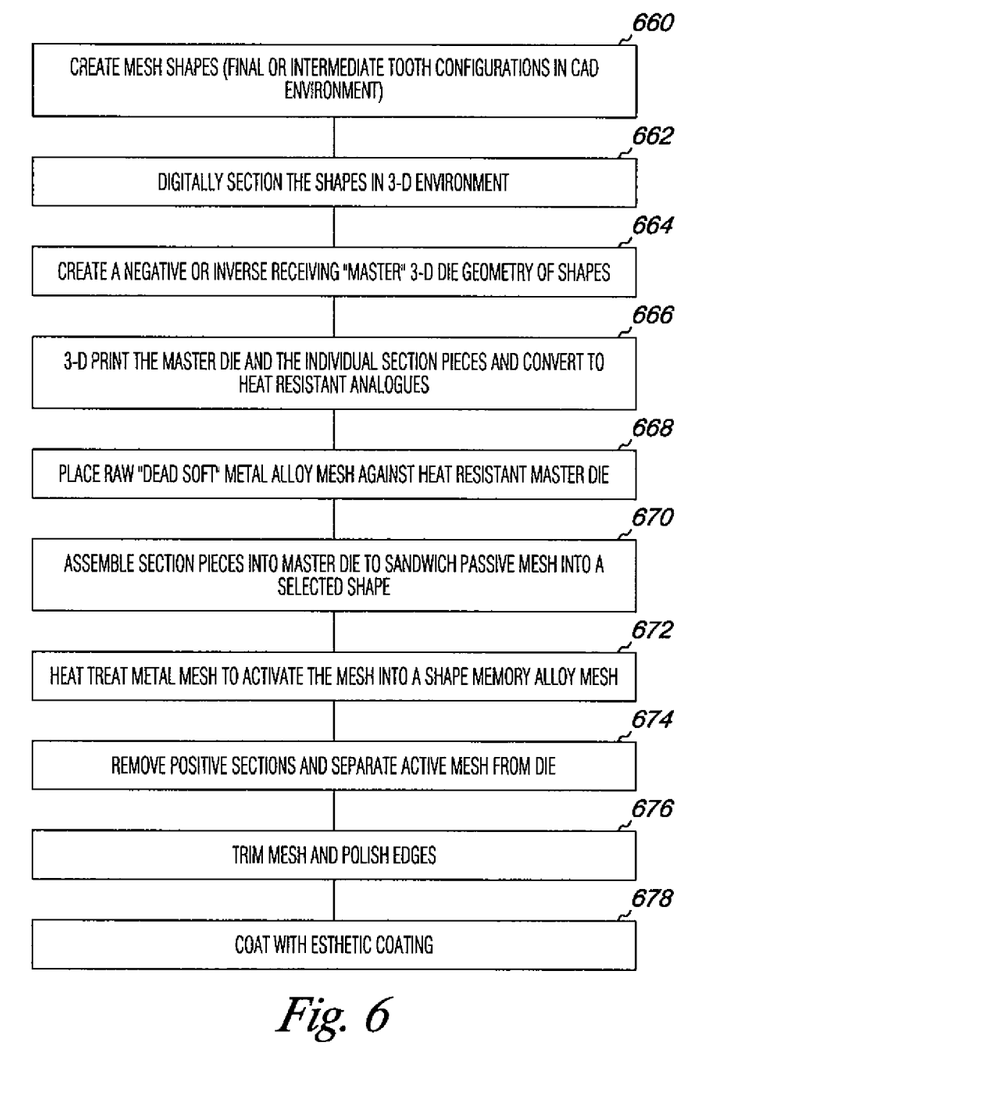
FIG. 6 illustrates a method for forming an appliance according to one or more embodiments of the present disclosure.

FIG. 6 illustrates a method for forming an appliance according to one or more embodiments of the present disclosure. Although discussed with respect to a mesh material, FIG. 6 should be interpreted to be suitable for metallic materials in generally and not limited to mesh materials.

In the embodiment of FIG. 6, the method includes creating one or more mesh shapes at block 660. The mesh shapes can be final or intermediate tooth configurations and can, for example, be created with a computing device aided drafting (CAD) program in two or three dimensions. In some embodiments, the mesh shapes may conform exactly to the shape of the teeth in the entire arch or may conform exactly only to a portion of the teeth in the arch, among other configurations.

In some embodiments, and as illustrated at block 662, the method of FIG. 6 includes digitally sectioning the mesh shapes in a 3-D environment. The digital sectioning of the mesh shapes can be used to create different dies for different metallic portions of the appliance if suitable for manufacturing.

Block 664 includes creating a computerized negative or inverse receiving die geometry of shapes. In the embodiment of FIG. 6, the die geometry is a computerized master 3-D type of die that can be used for forming multiple appliance dies.

At block 666, the master die and individual section pieces (e.g., forming mechanism portions) are printed and heat resistant forms are created. Forming one or more dies can include forming at least one die from a metallic or ceramic material.

In the embodiment illustrated in FIG. 6, raw metal alloy mesh is positioned against the master die at block 668. The sections are then assembled to sandwich the material into a selected shape at block 670. The metallic material can then be heat treated, if desired to create a shape memory alloy as discussed at block 672.

At block 674, the sections are removed and the formed metallic material is separated from the die. In such embodiments, the material can then be trimmed and/or polished, if desired, as indicated at block 676. In some embodiments, as illustrated at block 678, a coating can be added.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method of forming a dental positioning appliance, the method comprising:
   forming one or more dies based upon a machine readable three dimensional model of at least one physical tooth to be moved;
   applying at least a first wire and a second wire onto at least one of the dies;
   shaping at least the first wire and the second wire via interaction with each of the dies to form a mesh of a dental positioning appliance conforming to an inside, outside, and biting surface of the at least one physical tooth to be moved; and
   after the shaping, coating at least portions of the first wire and portions of the second wire including at least one junction thereof where at least the first wire and the second wire cross.

2. The method of claim 1, where shaping at least the first wire and the second wire includes pressing the first wire and the second wire between at least two of the dies.

3. The method of claim 1, where forming one or more dies includes forming at least one die from at least one material selected from the group including: metallic and ceramic materials.

4. The method of claim 1, where the method includes applying a coating to at least a portion of the appliance.

5. The method of claim 1, where the method includes heating the metallic material to change the material into a shape memory material.

6. The method of claim 1, where the method includes trimming one or more edges of the appliance.

7. The method of claim 1, where the method includes polishing one or more portions of the appliance.

8. The method of claim 1, where shaping the first wire and the second wire includes bending the first wire and the second wire into contact with at least one of the dies.

9. A method of forming a removable dental positioning appliance, the method comprising:
   applying at least a first wire and a second wire onto at least one die formed based upon a machine readable three dimensional model of at least one physical tooth to be moved;
   shaping at least the first wire and the second wire via interaction with each of the dies to form a mesh of a dental positioning appliance conforming to an inside, outside, and biting surface of the at least one physical tooth to be moved; and
   after the shaping, coating at least portions of the first wire and portions of the second wire including at least one junction thereof where at least the first wire and the second wire cross.

10. The method of claim 9, including forming a first portion of the appliance using a non-metallic, wherein at least the first wire and the second wire form a second portion of the removable dental positioning appliance.

11. The method of claim 9, wherein the first portion includes a first cavity and the second portion includes a second cavity, wherein at least the first cavity and the second cavity are formed to be placed over a number of teeth to be moved during a treatment period.

12. The method of claim 9, forming a mesh from at least the first wire and the second wire woven to create the mesh.

13. The method of claim 9, wherein applying the coating includes applying the coating directly on at least the first wire and the second wire along an inner surface of the dental appliance, the coating configured to contact a surface of one or more teeth of the patient.

14. The method of claim 9, wherein applying the coating includes applying the coating directly on only at least the first wire and the second wire along an outer surface of the removable dental positioning appliance.

15. The method of claim 12, wherein applying the coating includes applying the coating on only at least the first wire and the second wire along an inner surface of the removable dental positioning appliance.

* * * * *